United States Patent
Mason et al.

(10) Patent No.: US 9,700,279 B2
(45) Date of Patent: Jul. 11, 2017

(54) HANDS-FREE STETHOSCOPE

(71) Applicant: Sound the Bell, LLC, Burley, ID (US)

(72) Inventors: Curtis Angus Mason, Heyburn, ID (US); Victor Eugene Claridge, Rupert, ID (US); Norma Jean Trevino Claridge, Rupert, ID (US)

(73) Assignee: Sound the Bell, LLC, Burley, ID (US)

( * ) Notice: Subject to any disclaimer, the term of this patent is extended or adjusted under 35 U.S.C. 154(b) by 31 days.

(21) Appl. No.: 14/701,336

(22) Filed: Apr. 30, 2015

(65) Prior Publication Data
US 2016/0317117 A1  Nov. 3, 2016

(51) Int. Cl.
*A61B 5/02* (2006.01)
*A61B 7/04* (2006.01)
*A61B 5/024* (2006.01)
*A61B 5/00* (2006.01)

(52) U.S. Cl.
CPC ............ *A61B 7/04* (2013.01); *A61B 5/02411* (2013.01); *A61B 5/7203* (2013.01)

(58) Field of Classification Search
CPC ..... A61B 7/04; A61B 5/02411; A61B 5/7203; A61B 8/0866; A61B 5/02
See application file for complete search history.

(56) References Cited

U.S. PATENT DOCUMENTS

| | | | |
|---|---|---|---|
| 4,898,179 A * | 2/1990 | Sirota | A61B 7/04 381/67 |
| 8,121,305 B2 * | 2/2012 | Servello | H04R 1/02 381/77 |
| 8,571,603 B2 | 10/2013 | Carmody | |
| 2002/0155890 A1 | 10/2002 | Ha et al. | |
| 2013/0157763 A1 | 6/2013 | Joynes et al. | |
| 2013/0169069 A1 | 7/2013 | Stone et al. | |
| 2014/0049469 A1 | 2/2014 | Bragin | |
| 2014/0129755 A1 | 5/2014 | Jadhav et al. | |

(Continued)

FOREIGN PATENT DOCUMENTS

| | | |
|---|---|---|
| CN | 203167023 | 8/2013 |
| WO | 2012083484 | 6/2012 |

OTHER PUBLICATIONS

Discover in Details All the Specs 2013-2014 6.1 Gametab-One http://gametab-one.com/technical-specs/.

*Primary Examiner* — Mallika D Fairchild
(74) *Attorney, Agent, or Firm* — Workman Nydegger (57) ABSTRACT

Embodiments are directed to detecting the effect of external auditory sounds on a subject using a hands-free stethoscope, and further playing back those external auditory sounds as they are experienced inside a subject's body. A system is provided which includes a microphone that detects auditory sounds that are external to the system, and a stethoscope diaphragm that detects sound waves emitted within or as experienced in a subject's body. The stethoscope diaphragm also transfers a representation of those sound waves to a processor or to a headphone jack for playback. The processor of the system receives the representation of sound waves and also receives the detected external auditory sounds to determine what effect the detected external auditory sounds are having on the subject or on a second subject. The system also includes a communications module configured to communicate the results of the determination with other electronic devices.

18 Claims, 8 Drawing Sheets

(56) References Cited

U.S. PATENT DOCUMENTS

| | | | |
|---|---|---|---|
| 2014/0146464 A1 | 5/2014 | Abdelsamie et al. | |
| 2014/0364755 A1* | 12/2014 | Sankai | A61B 7/02 600/513 |
| 2015/0018635 A1* | 1/2015 | Dinesen | A61B 7/00 600/301 |

* cited by examiner

HANDS-FREE STETHOSCOPE

BACKGROUND

Stethoscopes are traditional medical instruments that allow doctors and other healthcare professionals to listen to sounds within a patient's body. The doctor typically holds the listening piece (with a bell and diaphragm) up the patient's heart or lungs or other area to listen to sounds within the body that cannot be heard externally. The sounds are transmitted through the listening piece up through a binaural earpiece to the doctor's ears. These sounds may give the doctor an idea of what is going on within the patient's body, and may be critical in providing a proper diagnosis. In some cases, the stethoscope may be entirely mechanical. In other cases, the stethoscope may include analog or digital parts.

BRIEF SUMMARY

Embodiments described herein are directed to detecting the effect of external auditory sounds on a subject using a hands-free stethoscope, and further playing back those external auditory sounds as they are experienced inside a subject's body. In one embodiment, a system is provided which includes multiple elements including a microphone configured to detect auditory sounds that are external to the system.

The system further includes a stethoscope diaphragm configured to detect sound waves emitted within or as experienced in a subject's body, and further transfer a representation of those sound waves to a processor or to a headphone jack for playback. The processor of the system is configured to receive the representation of sound waves from the stethoscope diaphragm, and further receive the detected external auditory sounds to determine what effect the detected external auditory sounds are having on the subject or on a second subject. The system also includes a communications module configured to communicate the results of the determination with other electronic devices.

In another embodiment, detecting the effect of external auditory sounds on a subject using the hands-free stethoscope is performed. The hands-free stethoscope detects auditory sounds that are external to the hands-free stethoscope and initializes a stethoscope diaphragm of the hands-free stethoscope to detect sound waves emitted within or as experienced in a subject's body. Then, based on the representation of sound waves from the stethoscope diaphragm and the detected external auditory sounds, the hands-free stethoscope determines what effect the detected external auditory sounds are having on the subject or on a second subject and communicates the results of the determination with other electronic devices.

In another embodiment, a hands-free stethoscope is provided which includes a microphone configured to detect auditory sounds that are external to the system, a stethoscope diaphragm configured to detect the external auditory sounds as experienced within a mother's body and transfer a representation of the external auditory sounds as experienced within the mother's body to a processor or to a speaker for playback. The processor of the hands-free stethoscope is configured to receive the representation of the external auditory sounds as experienced within the mother's body from the stethoscope diaphragm to determine what effect the detected external auditory sounds are having on the mother or on a baby within the mother.

Then, upon determining that the detected external auditory sounds are having a desired effect upon the mother or upon the baby, the processor instructs the detected external auditory sounds as experienced within the mother's body to be played back through the speaker. The hands-free stethoscope also includes a communications module configured to communicate the results of the determination with other electronic devices.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

Embodiments described herein are directed to detecting the effect of external auditory sounds on a subject using a hands-free stethoscope, and further playing back those external auditory sounds as they are experienced inside a subject's body. In one embodiment, a system is provided which includes multiple elements including a microphone configured to detect auditory sounds that are external to the system.

The system further includes a stethoscope diaphragm configured to detect sound waves emitted within or as experienced in a subject's body, and further transfer a representation of those sound waves to a processor or to a headphone jack for playback. The processor of the system is configured to receive the representation of sound waves from the stethoscope diaphragm, and further receive the detected external auditory sounds to determine what effect the detected external auditory sounds are having on the subject or on a second subject. The system also includes a communications module configured to communicate the results of the determination with other electronic devices.

In another embodiment, detecting the effect of external auditory sounds on a subject using the hands-free stethoscope is performed. The hands-free stethoscope detects auditory sounds that are external to the hands-free stethoscope and initializes a stethoscope diaphragm of the hands-free stethoscope to detect sound waves emitted within or as experienced in a subject's body. Then, based on the representation of sound waves from the stethoscope diaphragm and the detected external auditory sounds, the hands-free stethoscope determines what effect the detected external auditory sounds are having on the subject or on a second subject and communicates the results of the determination with other electronic devices.

In another embodiment, a hands-free stethoscope is provided which includes a microphone configured to detect auditory sounds that are external to the system, a stethoscope diaphragm configured to detect the external auditory sounds as experienced within a mother's body and transfer a representation of the external auditory sounds as experienced within the mother's body to a processor or to a speaker for playback. The processor of the hands-free stethoscope is configured to receive the representation of the external auditory sounds as experienced within the mother's body from the stethoscope diaphragm to determine what effect the detected external auditory sounds are having on the mother or on a baby within the mother.

Then, upon determining that the detected external auditory sounds are having a desired effect upon the mother or upon the baby, the processor instructs the detected external auditory sounds as experienced within the mother's body to be played back through the speaker. The hands-free stethoscope also includes a communications module configured to communicate the results of the determination with other electronic devices.

The following discussion now refers to a number of methods and method acts that may be performed. It should be noted, that although the method acts may be discussed in a certain order or illustrated in a flow chart as occurring in a particular order, no particular ordering is necessarily required unless specifically stated, or required because an act is dependent on another act being completed prior to the act being performed.

Embodiments described herein may implement various types of computing systems. These computing systems are now increasingly taking a wide variety of forms. Computing systems may, for example, be handheld devices such as smartphones or feature phones, appliances, laptop computers, wearable devices, desktop computers, mainframes, distributed computing systems, or even devices that have not conventionally been considered a computing system. In this description and in the claims, the term "computing system" is defined broadly as including any device or system (or combination thereof) that includes at least one physical and tangible hardware processor, and a physical and tangible hardware or firmware memory capable of having thereon computer-executable instructions that may be executed by the processor. For instance, the device 100 of FIG. 1 may comprise a computing system as it includes at least one processor. A computing system may be distributed over a network environment and may include multiple constituent computing systems.

A computing system, such as device 100, typically includes at least one processing unit and memory. The memory may be physical system memory, which may be volatile, non-volatile, or some combination of the two. The term "memory" may also be used herein to refer to non-volatile mass storage such as physical storage media or physical storage devices. If the computing system is distributed, the processing, memory and/or storage capability may be distributed as well.

As used herein, the term "executable module" or "executable component" can refer to software objects, routines, or methods that may be executed on the computing system. The different components, modules, engines, and services described herein may be implemented as objects or processes that execute on the computing system (e.g., as separate threads).

In the description that follows, embodiments are described with reference to acts that are performed by one or more computing systems. If such acts are implemented in software, one or more processors of the associated computing system that performs the act direct the operation of the computing system in response to having executed computer-executable instructions. For example, such computer-executable instructions may be embodied on one or more computer-readable media or computer-readable hardware storage devices that form a computer program product.

An example of such an operation involves the manipulation of data. The computer-executable instructions (and the manipulated data) may be stored in the memory of the computing system. The computing system may also contain communication channels that allow the computing system to communicate with other message processors over a wired or wireless network. Such communication channels may include hardware-based receivers, transmitters or transceivers, which are configured to receive data, transmit data or perform both.

Embodiments described herein may comprise or utilize a special-purpose or general-purpose computer system that includes computer hardware, such as, for example, one or more processors and system memory, as discussed in greater detail below. The system memory may be included within the overall memory. The system memory may also be referred to as "main memory", and includes memory locations that are addressable by the at least one processing unit over a memory bus in which case the address location is asserted on the memory bus itself. System memory has been traditionally volatile, but the principles described herein also apply in circumstances in which the system memory is partially, or even fully, non-volatile.

Embodiments described herein also include physical and other computer-readable media for carrying or storing computer-executable instructions and/or data structures. Such computer-readable media can be any available media that can be accessed by a general-purpose or special-purpose computer system. Computer-readable media or storage devices that store computer-executable instructions and/or data structures are computer storage media or computer storage devices. Computer-readable media that carry computer-executable instructions and/or data structures are transmission media. Thus, by way of example, and not limitation, embodiments described herein may comprise at least two distinctly different kinds of computer-readable media: computer storage media and transmission media.

Computer storage media are physical hardware storage media that store computer-executable instructions and/or data structures. Physical hardware storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the embodiments described herein.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the principles described herein may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The embodiments herein may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the embodiments herein may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

Still further, system architectures described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

Figure 1:
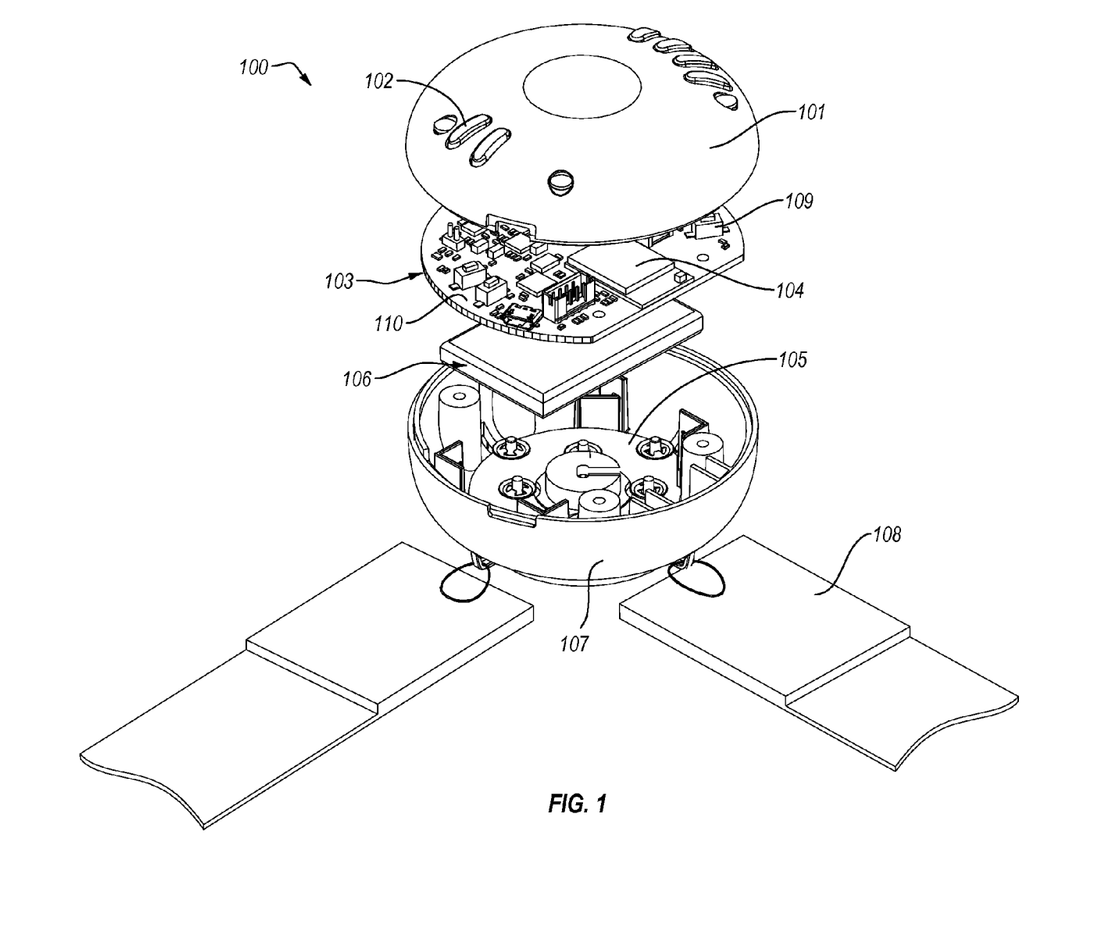
FIG. 1 illustrates an exploded view of an embodiment of a hands-free stethoscope.

FIG. 1 illustrates an exploded view of one embodiment of a hands-free stethoscope 100. The hands-free stethoscope 100 may include computing hardware including a processor 104. The computing hardware may be part of one or more printed circuit boards 103 which interconnect the electronic components. The hands-free stethoscope 100 may communicate with other computing systems using a communications module 110. The communications module 104 may include any wired or wireless communication means that can receive and/or transmit data to or from other computing systems. The communications module 104 may be configured to interact with databases, mobile computing devices (such as mobile phones or tablets), embedded or other types of computing systems. In one specific embodiment, the communications module 110 may be configured to communicate sound waves detected by the stethoscope diaphragm 105 to a speaker for playback or to another computing system for diagnostics, filtering or other signal processing.

The hands-free stethoscope 100 (also referred to as "the system" or "system 100" herein) may further include a microphone 109 configured to detect auditory sounds that are external to the system. For example, the microphone 109 may listen for music or a vacuum or the sound of a car engine or the sound of a person talking or singing or any number of sounds that may be recorded. In some cases, the processor 104 (or a processor on an external computer system) determines when an external sound has a positive effect on a baby still in vitro. The hands-free stethoscope 100 includes a stethoscope diaphragm 105 that detects sound waves emitted within or as experienced in a subject's body (e.g. an expectant mother's body). The diaphragm 105 then transfers a representation of those sound waves to the processor 104 or to a headphone jack for personal playback.

The processor 104 receives the representation of sound waves from the stethoscope diaphragm 105 and also accesses the detected external auditory sounds to determine what effect the detected external auditory sounds are having on the subject or on a second subject (e.g. on the mother and/or on the baby). The processor may determine, for example, that a baby's heartrate slows or quickens when certain external sounds or noises are present. Additionally or alternatively, the processor 104 may determine that the baby increases or decreases movement in response to certain external sounds. The communications module 110 may communicate the results of the determination with other electronic devices wirelessly, or over a wired connection.

In some embodiments, data from the hands-free stethoscope 100 may be transmitted to nearby devices that are connected via Bluetooth such as a smartphone, tablet or wearable device. The communications module 110 may include a Bluetooth, WiFi or other type of wireless radio. The wireless radio may be used to communicate heartbeat data, movement data or other types of data to other electronic devices. The heartbeat data may be recordable on the wired or wirelessly connected electronic devices, or may be stored on a storage module within the hands-free stethoscope 100. In some cases, the hands-free stethoscope 100 may be communicatively connected to a speaker for playback of the representation of sound waves. For instance, the stethoscope diaphragm 105 may detect sound waves and pass those through to a headphone jack, or may transmit the detected sound waves to a wired or wireless device such as a speaker or smart phone. As such, the speaker or smart phone may play the detected sound waves in real time.

The hands-free stethoscope 100 may further include one or more buttons 102 on the outer shell 101 such as those shown in FIG. 1. It will be understood, of course, that the hands-free stethoscope 100 may include substantially any number of buttons of any button type or shape. The buttons 102 may perform functions including turning power off or on to the hands-free stethoscope 100, starting or stopping the microphone 109, initiating or stopping transmission of sound waves over the communications module 110 or performing other functions. The hands-free stethoscope 100 may also include a battery 106 or perhaps a wired power source.

The hands-free stethoscope 100 may implement one or more straps 108 to secure itself to a certain portion of the user's body. For mothers, the straps may be used to secure the hands-free stethoscope 100 to their belly so as to listen to the sounds coming from their baby. For other users, the straps 108 may be used to secure the stethoscope to their chest to monitor breathing or heart function, or to their bowels to monitor bowel function, or to other areas of interest. While straps are shown in FIG. 1 as being usable to fasten the hands-free stethoscope to a person's body or other object, it will be understood that substantially any type of fastening mechanism may be used including clips, buttons, Velcro, tie-down strings or cords or other types of fasteners. In some cases, a plurality of different fasteners may be used on the same device.

In cases where the hands-free stethoscope 100 is used by an expectant mother to monitor her baby, the hands-free stethoscope 100 (or a communicatively linked smartphone) may be configured to record any external sounds and record the baby's response thereto. The stethoscope diaphragm 105 may further be used to record the external sound as it is heard through the mother's body. In other words, the stethoscope diaphragm may detect the sound waves from an external source such as a treadmill or a vacuum or a violin as they would be heard by the baby, in a muffled, removed fashion. These sound waves detected by the stethoscope diaphragm 105 may then be recorded and later played back through an external or built-in speaker. For instance, when the baby is born, those sounds that were determined to be pleasing to the infant while in vitro may be played back in the manner they would have been heard by the baby while in vitro. This may have a soothing effect on the baby, similar to the effect detected before the baby was born.

Figure 2:
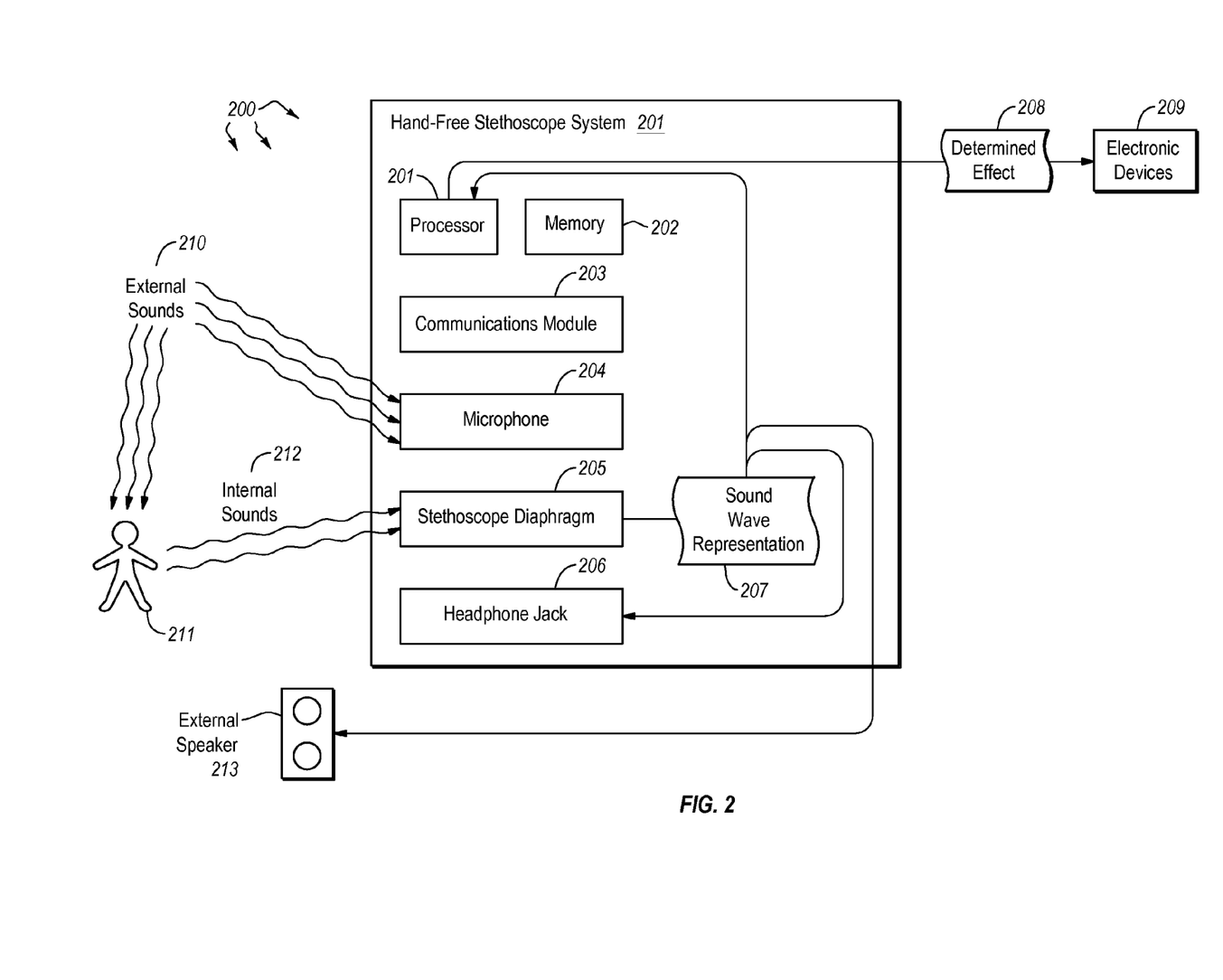
FIG. 2 illustrates a computer architecture in which embodiments described herein may operate including detecting the effect of external auditory sounds on a subject using a hands-free stethoscope.

Turning now to FIG. 2, a computing architecture 200 is shown. The computing architecture includes a hands-free stethoscope 201 which may be similar to or the same as that shown in FIG. 1. The hands-free stethoscope 201 may include a processor 201 and memory 202, along with other hardware components including a communications module 203. The communications module may include wireless or wired means of communicating with other electronic devices. The hands-free stethoscope 201 further includes a microphone 204 that is capable of detecting external sounds 210. As mentioned above, the external sounds 210 may be any type of music, white noise, speaking, singing or other type of sound. The external sounds may be heard by a user 211 such as an expectant mother. The external sounds may also be heard by a baby inside the mother, albeit in a more subdued or distorted manner. In some cases, the microphone 204 may be accompanied by one or more other microphones that may be used for noise cancelling or noise reduction or for other similar purposes.

The stethoscope diaphragm 205 of the hands-free stethoscope 201 may be placed over the user 211's body to listen to internal sounds such as breathing, heartbeat, or other internal sounds including those related to a baby if present. Indeed, the hands-free stethoscope 201 may be used on men and non-pregnant women and children to listen to internal bodily functions. The internal sounds 212 detected by the stethoscope diaphragm 205 may be transmitted to headphone jack 206, to processor 201 and/or to external speaker 213. The transmitted sound wave representation 207 may include the heartbeats, breathing or other noises.

In the case of pregnant women, the sound wave representation may also include sounds from the baby and, if external sounds 210 are playing, the muted form of those sounds as heard through the stethoscope diaphragm 205. In these cases where the hands-free stethoscope 201 is strapped to an expectant mother, and where external sounds 210 such as music or singing are playing, the processor 201 may monitor the infant's heartrate or breathing rate, and may determine that the external sounds 210 are having an effect on the baby. This determined effect 208 may be sent to one or more electronic devices 209. The sound wave representation 207 may also be sent to the electronic devices such as a smart phone belonging to the user 211 or to a smart phone belonging to a doctor or nurse.

In some embodiments, the external sounds 210 that had the most calming effects on the infant may be stored in a data store. This data store may be internal to or external to the hands-free stethoscope 201. The stored sounds may then be played back once the baby is outside of the womb with the intent that those sounds that calmed the baby in the womb will also calm the baby once he or she is out of the womb. In cases where the hands-free stethoscope 201 is used on other non-pregnant users, the sounds of their heartbeat or breathing or bowels may also be stored in the data store, and may be played back by the user 211 or by a doctor or nurse. One of the buttons 102 shown in FIG. 1 may be used to initiate recording of the sound waves emitted within the user's body. The recorded data may be stored in the data store. In cases where the data store is external to the system, the data may be accessible using the communications module 203 (e.g. when the data is stored in a cloud data store). In addition to the buttons 102, the hands-free stethoscope 201 may also include a digital display for displaying system features and controls. The user 211 may use this digital display (which may be a touchscreen) to control recording, playback and other features.

Figure 3:
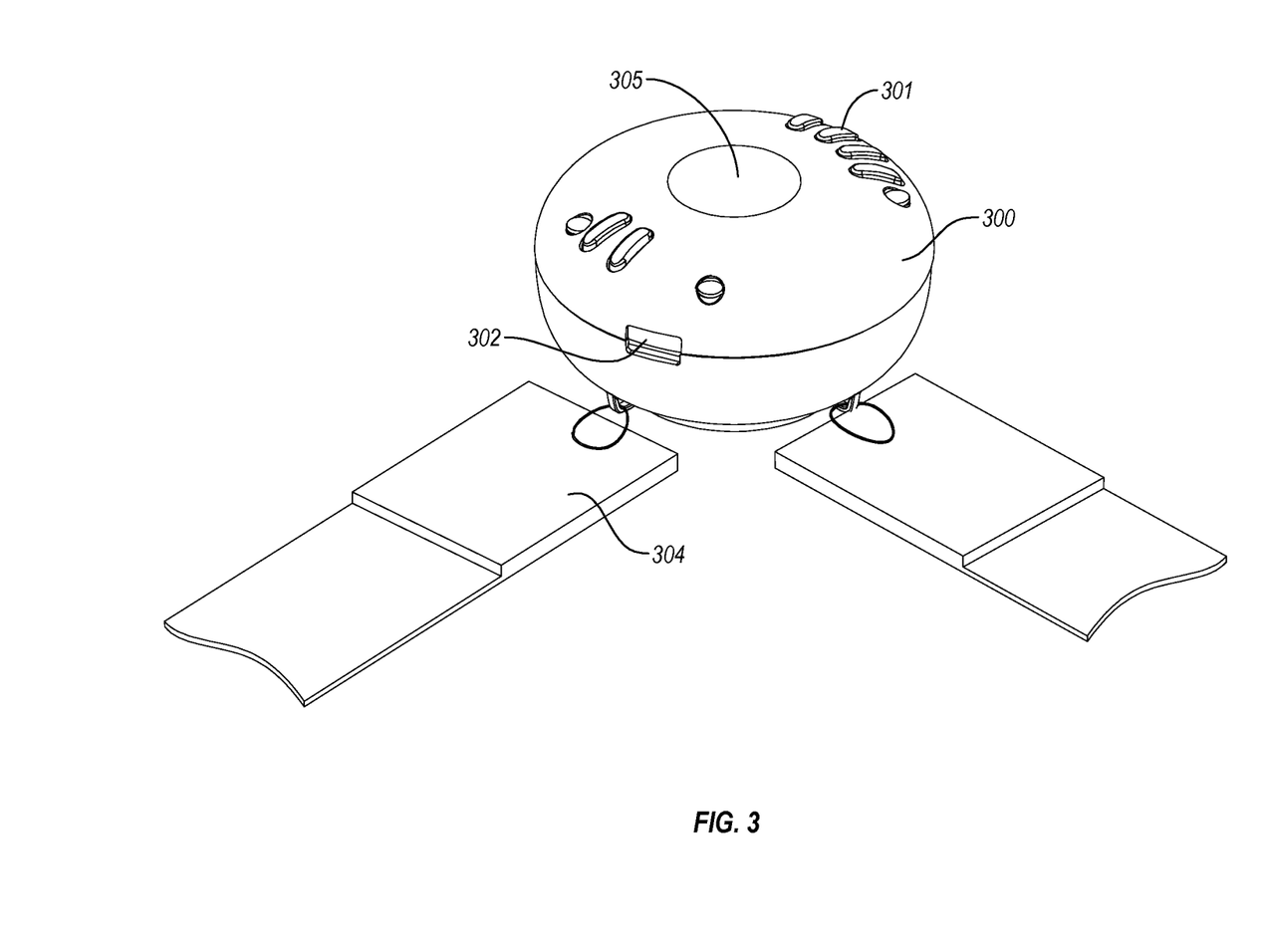
FIG. 3 illustrates a perspective view of an embodiment of a hands-free stethoscope.

FIG. 3 illustrates a perspective view of a hands-free stethoscope 300 which may include straps 304 for strapping the hands-free device to a person's body. In some cases, only one strap is included, while in other cases, two or more straps may be used to hold the hands-free stethoscope 300 securely against the body so that measurements can be taken without having to hold the stethoscope in place. The hands-free stethoscope 300 may include a speaker 305 at the top or elsewhere on the device for playing back the sounds detected by the diaphragm. The hands-free stethoscope 300 may also include buttons 301 for performing various functionality including turning the diaphragm on and off, as well as turning the device on or off or pairing the device with other external devices such as smart phones or speakers. The hands-free stethoscope may have indicators or a digital display showing the current state of different forms of functionality. Still further, the hands-free stethoscope 300 may include a communications port 302 such as a USB port or other type of interface that allows wired communication with other electronic devices.

Figure 4:
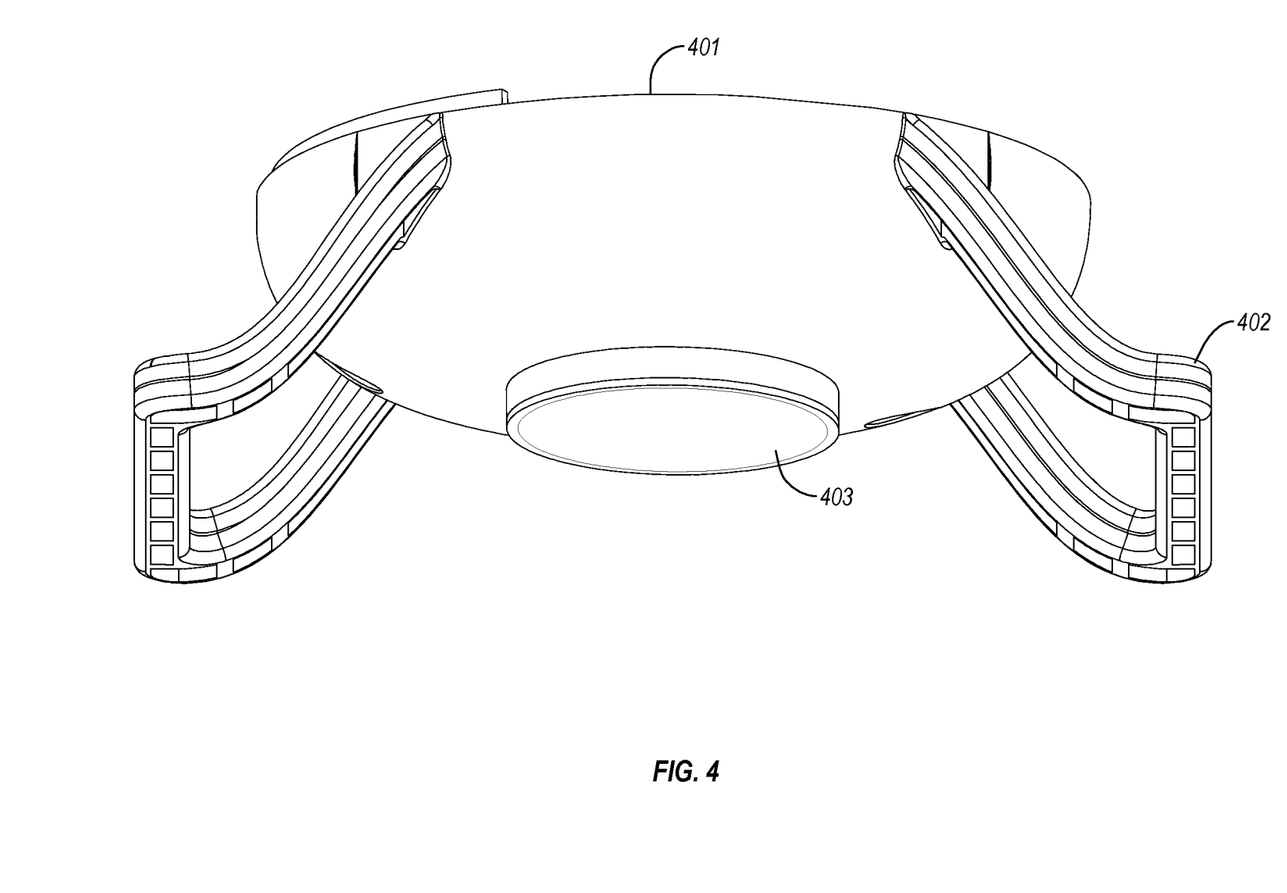
FIG. 4 illustrates a side view of an embodiment of the bottom half of a hands-free stethoscope.

FIG. 4 illustrates a perspective view of the bottom half of a hands-free stethoscope. The supports 402 may rest against the user's body, and may also allow the straps to slide through to secure the stethoscope to the individual's body. When secured against the body, the stethoscope diaphragm 403 will also be pressed against the individual's body so that the internal noises can be properly detected by the diaphragm 403. The bottom shell 401 provides structure for the device and a housing for the internal components. It will be understood that this is just one embodiment of a housing with supports and a diaphragm, and that other designs and shapes may also be used.

Figure 5:
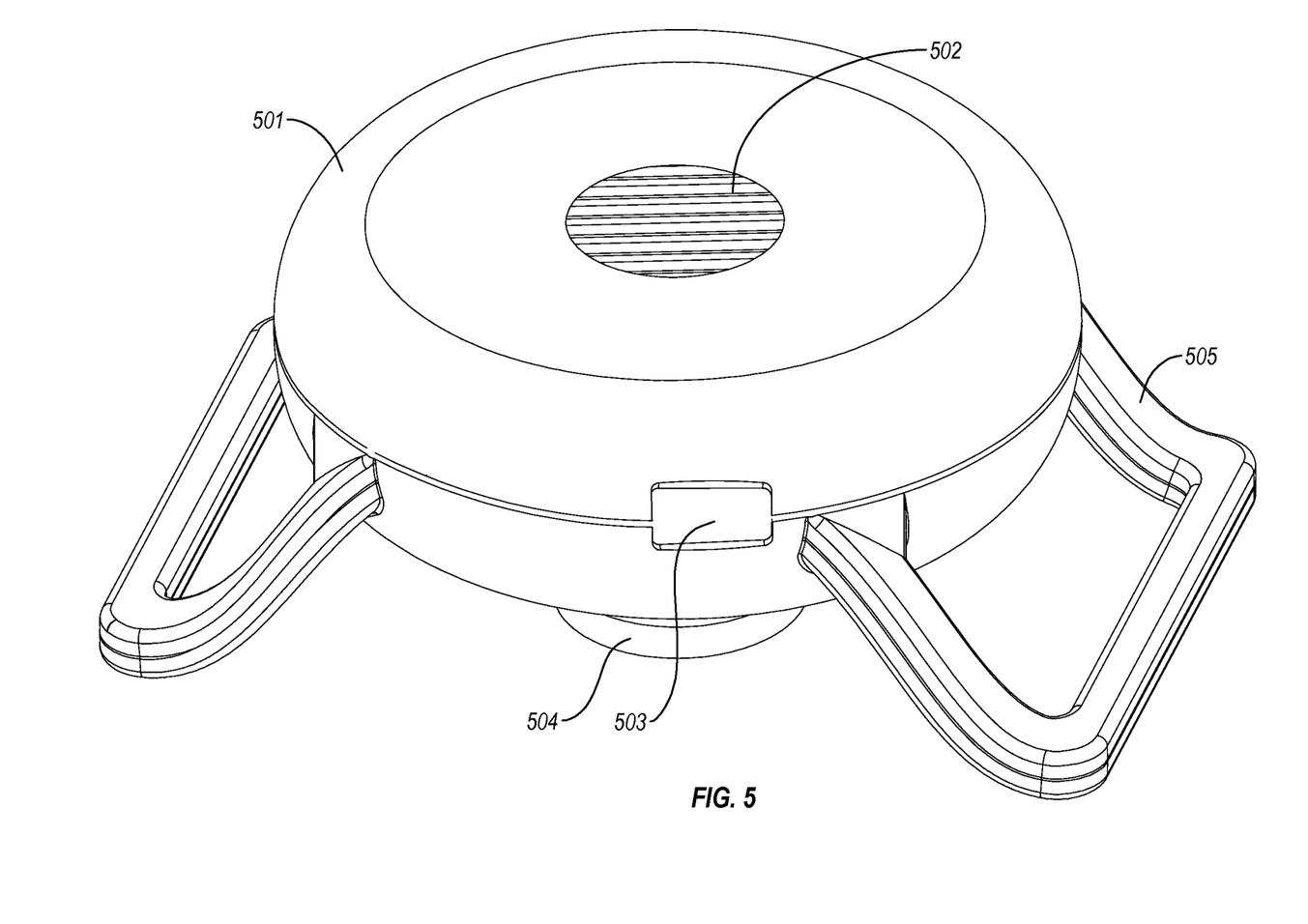
FIG. 5 illustrates an alternative perspective view of an embodiment of a hands-free stethoscope.

FIG. 5 illustrates a perspective view of a hands-free stethoscope 501 that includes features similar to those shown in FIG. 3. The hands-free stethoscope 501 includes a speaker or microphone 502 for playing or detecting sounds. The hands-free stethoscope 501 also includes a communications port 503 and a diaphragm 504 for detecting internal sounds. The hands-free stethoscope 501 further includes supports 505 for connecting the brace to the body of the stethoscope. In some cases, the hands-free stethoscope 501 may further include a connecting member that allows the hands-free stethoscope to connect to standard stethoscope binaural earpiece. The connecting member could be on the side (e.g. next to communications port 503), on the top or on the bottom of the device. The connecting member would allow a nurse, doctor or other user to connect a standard binaural earpiece to the hands-free stethoscope 501 to allow the user to listen to the sounds detected by the diaphragm 504.

Figure 6:
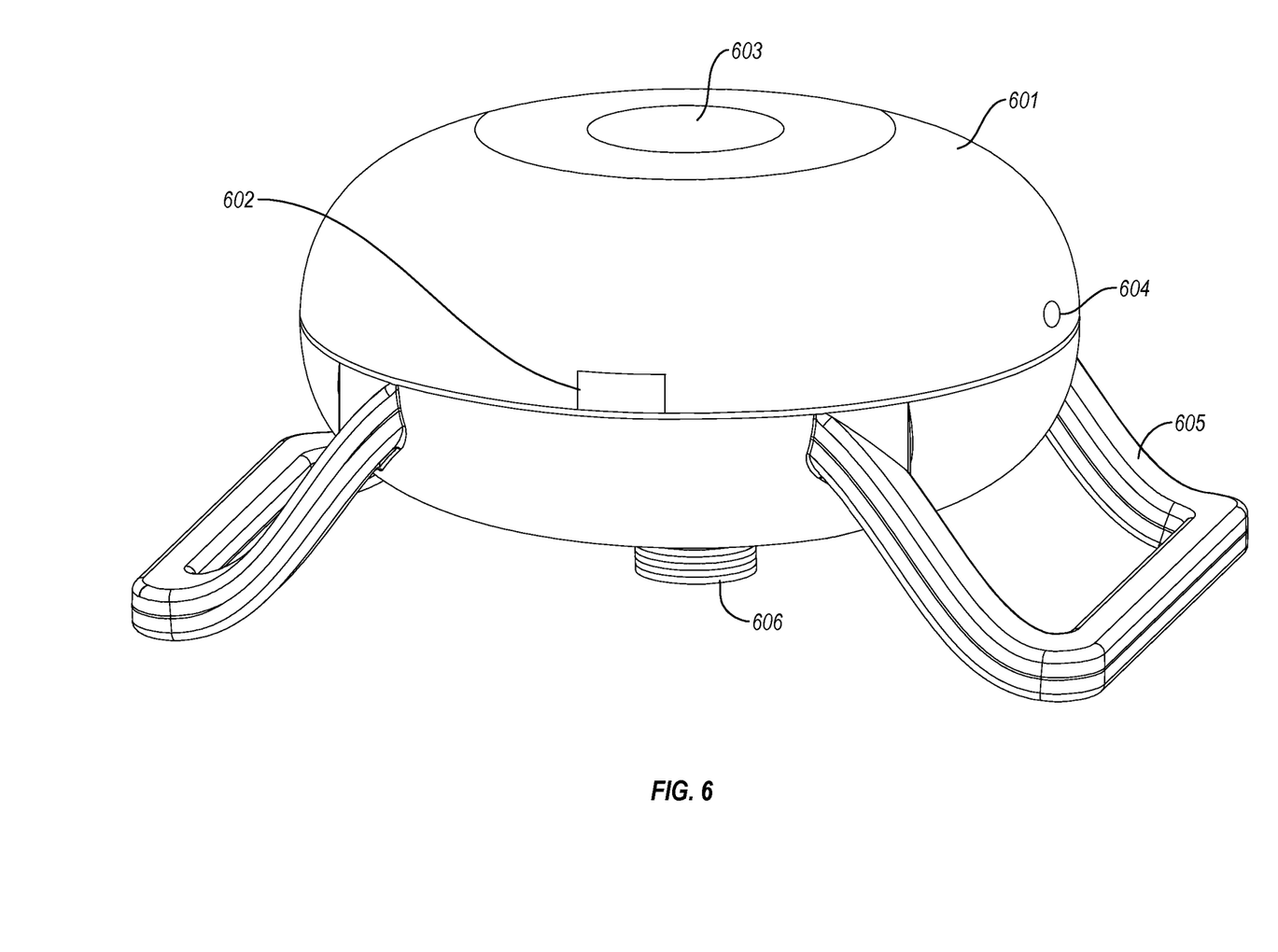
FIG. 6 illustrates an alternative perspective view of an embodiment of a hands-free stethoscope.

FIG. 6 illustrates an embodiment in which a hands-free stethoscope 601 includes an interchangeable diaphragm 606. As indicated by the thread patterns, a diaphragm may be added or removed from the hands-free stethoscope 601 by a user. This allows different diaphragms to be used when needed or desired. The hands-free stethoscope 601 may include a communications port 602, as well as a headphone jack 604. Similarly, the hands-free stethoscope 601 may include a speaker/microphone 603 and support structures 605.

Figure 7:
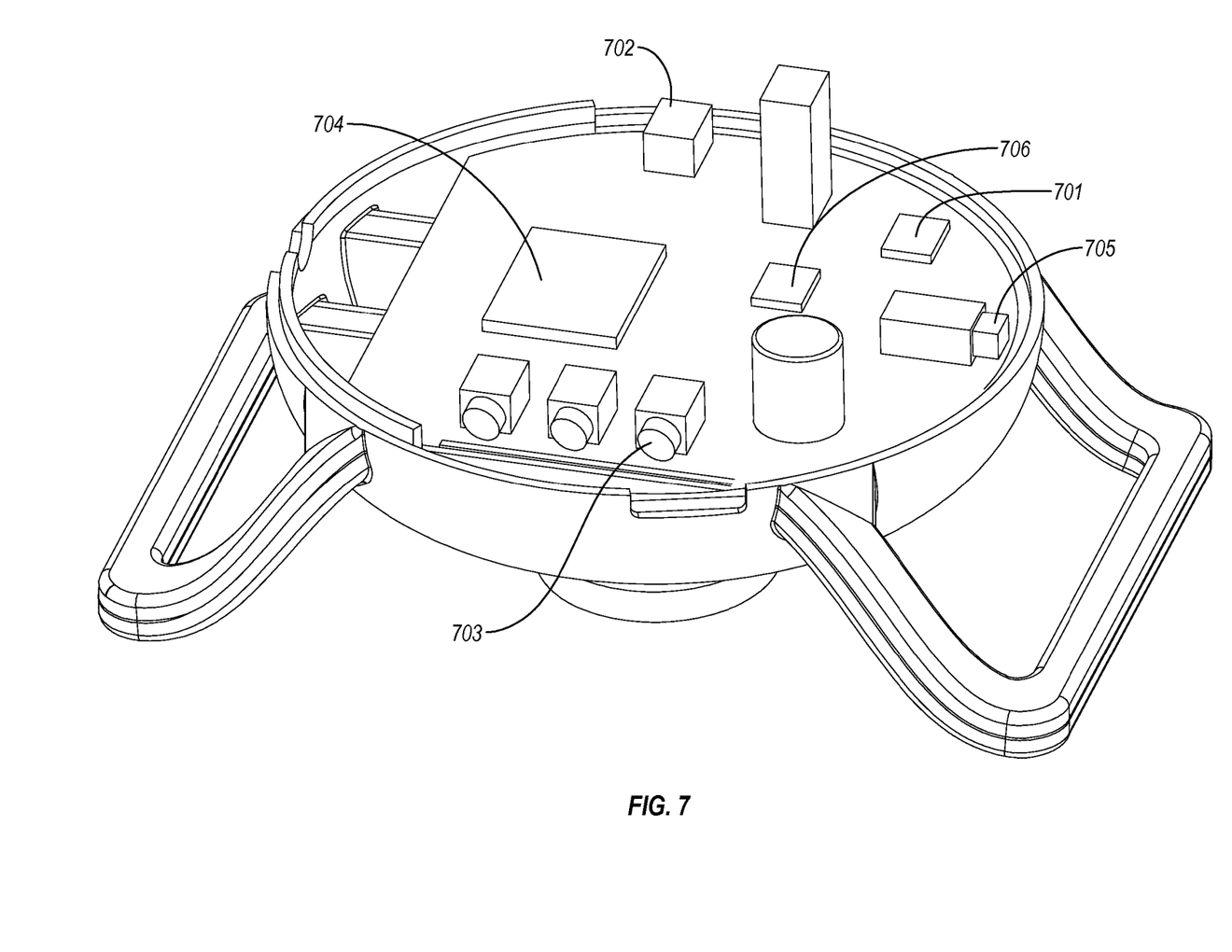
FIG. 7 illustrates a perspective view of an embodiment of a hands-free stethoscope including a view of one or more internal components of the stethoscope.

FIG. 7 illustrates some of the internal components which may be in place inside a hands-free stethoscope such as those shown in FIGS. 1 and 3-6. The hands-free stethoscope may include buttons or indicators 703 on the front facing side, as well as a processor 704. The hands-free stethoscope may further include a wireless radio 701 and data store 706, along with communications port 702 and headphone port 705. Many other components may be included or omitted from those shown. Indeed, the hands-free stethoscope may include an onboard amplifier that amplifies the representation of sound waves prior to transferring the representation of sound waves to the speaker for playback. The hands-free stethoscope may also include a signal filter that filters sound waves representations for specified patterns or characteristics. The filtering may thus take place on the device, or may be passed to an external device such as a laptop or smartphone for processing.

In one specific embodiment, hands-free stethoscope includes the following: a microphone configured to detect auditory sounds that are external to the device. The hands-free stethoscope further includes a stethoscope diaphragm configured to detect the external auditory sounds as experienced within a mother's body and transfer a representation of the external auditory sounds as experienced within the mother's body to a processor for processing or to a speaker for playback. The processor may receive the representation of the external auditory sounds as experienced within the mother's body from the stethoscope diaphragm to determine what effect the detected external auditory sounds are having on the mother or on a baby within the mother. Then, upon determining that the detected external auditory sounds are having a desired effect upon the mother or upon the baby, the processor may instruct the detected external auditory sounds as experienced within the mother's body to be played back through the speaker concurrently or at a later time. The hands-free stethoscope further includes a communications module that communicates the results of the determination with one or more other electronic devices.

Figure 8:
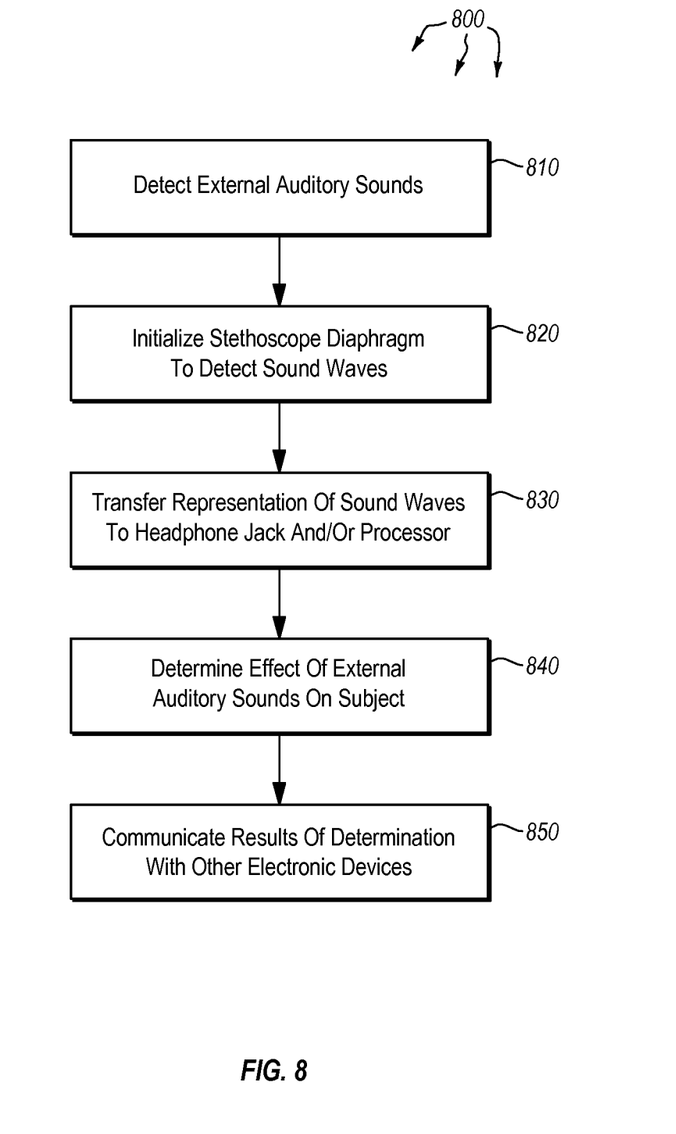
FIG. 8 illustrates a flowchart of an example method for detecting the effect of external auditory sounds on a subject using a hands-free stethoscope.

Turning now to FIG. 8, in view of the systems and architectures described above, methodologies that may be implemented in accordance with the disclosed subject matter will be better appreciated with reference to the flow charts of FIG. 8. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 8 illustrates a flowchart of a method 800 for detecting the effect of external auditory sounds on a subject using the hands-free stethoscope. The method 800 will now be described with frequent reference to the components and data of environment 200 of FIG. 2.

Method 800 includes detecting one or more auditory sounds that are external to the hands-free stethoscope (810). For example, microphone 204 may detect external sounds 210 emitted from a speaker, a device, a person or other object. Method 800 next includes initializing a stethoscope diaphragm of the hands-free stethoscope to detect sound waves emitted within or as experienced in a subject's body (820). The hands-free stethoscope system 201 may (perhaps in response to a user pressing a button) initialize the stethoscope diaphragm 205 to detect sound waves 212 emitted with or as experienced in user 211's body. The detected sounds waves may include internal noises, or may include internal noises plus a muted form of the external sounds 210 emitted outside of the hands-free stethoscope system 201.

Method 800 next includes transferring a representation of the detected sound waves to at least one of a headphone jack or to a processor of the hands-free stethoscope (830). The stethoscope diaphragm 205 may be electronically connected to the processor 201 and/or to the external speaker 213 or other electronic devices 209. The stethoscope diaphragm 205 may thus transmit the detected sound wave representations 207 to the processor, external speaker or external electronic devices for processing, playback and/or storage. Based on the representation of sound waves 207 from the stethoscope diaphragm 205 and the one or more detected external auditory sounds 210, the processor 201 may determine what effect the detected external auditory sounds are having on the subject or on a second subject (840).

For example, the processor may determine that the external sounds are exciting the mother or baby because their heart rates have increased. Similarly, the processor may determine that the external sounds 210 are calming the mother or baby because their heart rates or breathing rates have decreased, or because their movements have decreased. The results of the determination 208 may then be communicated with other electronic devices (850). In cases where the external sounds had a calming effect, the external sound may be stored as heard by the microphone 204 and/or as heard through the womb as detected by the stethoscope diaphragm 205. Thus, if the processor 201 determines that detected external auditory sounds are having a desired effect on the mother or baby, those sounds may be played back through a speaker as experienced within the subject's body.

The hands-free stethoscope system 201 may be configured to store, play and manage data files directly on the device, or through an interface that allows control of a connected electronic device 209. Indeed, in some cases, the hands-free stethoscope may be synchronized with at least one other electronic device such as a tablet or phone. The synchronizing may allow data transfer between the hands-free stethoscope and the other electronic device. In some cases, detected sound waves emitted within or as experienced in the subject's body may be automatically transferred to the synchronized device for playback and/or storage. In still other cases, the detected sound waves emitted within the subject's body may be communicated to a display that is used to show a visual representation of the detected sound waves (heartbeat, lung, voice, etc.). Thus, in this manner, a hands-free stethoscope may be used to monitor, store and replay sounds as heard within the body and, more specifically, may replay sounds that are known to sooth a baby while in or out of the mother's womb.

Accordingly, a hands-free stethoscope is described herein which detects the effect of external auditory sounds on a subject. Moreover, methods, systems and computer program products are provided which detects the effect of external auditory sounds on a subject using the hands-free stethoscope.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

We claim:

1. A system comprising:
 a speaker;
 a microphone configured to detect one or more auditory sounds that are external to the system;
 a stethoscope diaphragm configured to detect sound waves emitted within or as experienced in a subject's body and transfer a representation of those sound waves to at least one of a processor or to the speaker for playback;
 the processor configured to receive and record the representation of sound waves from the stethoscope diaphragm and receive the one or more detected external auditory sounds to determine what effect the detected external auditory sounds are having on the subject or on a second subject, wherein upon determining that a specified external auditory sound has had a specified effect, replaying through the speaker a recording of the specified external auditory sound as detected in the subject's body by the stethoscope diaphragm; and
 a communications module configured to communicate results of the determination with one or more other electronic devices.

2. The system of claim 1, wherein the communications module comprises a wireless communications module configured to wirelessly communicate with other electronic devices.

3. The system of claim 2, wherein the wireless communications module communicates heartbeat data to the other electronic devices.

4. The system of claim 3, wherein the heartbeat data is recordable on the other electronic devices or on a storage module within the system.

5. The system of claim 1, wherein the system is communicatively connected to a speaker for playback of the representation of sound waves.

6. The system of claim 1, wherein the system further includes at least one strap adapted to physically secure the system to the subject for hands-free stethoscope functionality.

7. The system of claim 1, further comprising at least one button that, when activated, initiates recording of the sound waves emitted within the subject's body in a data store.

8. The system of claim 7, wherein the data store is located within the system, or is external to the system and is accessible using the communications module.

9. The system of claim 1, further comprising a digital display for displaying system features and controls.

10. A method, implemented at a hands-free stethoscope that includes at least one strap adapted to physically secure the hands-free stethoscope to a subject for hands-free stethoscope functionality and at least one processor, for detecting the effect of external auditory sounds on the subject using the hands-free stethoscope, the method comprising:
 detecting one or more auditory sounds that are external to the hands-free stethoscope;
 initializing a stethoscope diaphragm of the hands-free stethoscope to detect sound waves emitted within or as experienced in a subject's body;
 transferring a representation of the detected sound waves to at least one of a speaker or to a processor of the hands-free stethoscope for recording of the detected sound waves;
 based on the representation of sound waves from the stethoscope diaphragm and the one or more detected external auditory sounds, determining that the detected external auditory sounds are having a specified effect on the subject or on a second subject;

playing back a recording of the detected external auditory sounds as detected in the subject's body by the stethoscope diaphragm through the speaker; and communicating the results of the determination with one or more other electronic devices.

11. The method of claim 10, wherein the hands-free stethoscope is configured to store, play and manage data files.

12. The method of claim 10, further comprising synchronizing the hands-free stethoscope with at least one other electronic device, the synchronizing allowing data transfer between the hands-free stethoscope and the at least one other electronic device.

13. The method of claim 12, wherein the detected sound waves emitted within or as experienced in the subject's body are transferred to the synchronized device for playback or storage.

14. The method of claim 12, wherein the detected sound waves emitted within the subject's body are communicated to a display that is configured to show a visual representation of the detected sound waves.

15. A hands-free stethoscope, comprising:
- at least one strap adapted to physically secure the hands-free stethoscope to a mother's body for hands-free stethoscope operation;
- a microphone configured to detect one or more auditory sounds that are external to the system;
- a stethoscope diaphragm configured to detect the external auditory sounds as experienced within the mother's body and transfer a representation of the external auditory sounds as experienced within the mother's body to at least one of a processor or to a speaker for playback;
- the processor configured to receive and record the representation of the external auditory sounds as experienced within the mother's body from the stethoscope diaphragm to determine what effect the detected external auditory sounds are having on the mother or on a baby within the mother and, upon determining that the detected external auditory sounds are having a specified effect upon the mother or upon the baby, instructing a recording of the detected external auditory sounds as detected in the mother's body by the stethoscope diaphragm to be played back through the speaker; and
- a communications module configured to communicate the results of the determination with one or more other electronic devices.

16. The hands-free stethoscope of claim 15, further comprising a connecting member that allows the hands-free stethoscope to connect to a standard stethoscope binaural earpiece.

17. The hands-free stethoscope of claim 15, further comprising an onboard amplifier configured to amplify the representation of the external auditory sounds prior to transferring the representation of the external auditory sounds to the speaker for playback.

18. The hands-free stethoscope of claim 15, further comprising a signal filter configured to filter representation of the external auditory sounds for one or more specified patterns or characteristics.

* * * * *